United States Patent
Hefner, Jr. et al.

(10) Patent No.: US 12,030,836 B2
(45) Date of Patent: Jul. 9, 2024

(54) PHENYL ISOCYANATE CONVERSION PROCESS

(71) Applicants: Dow Global Technologies LLC, Midland, MI (US); Dow Portugal Produtos Quimicos, Sociedade Unipessoal, LDA, Estarreja (ES)

(72) Inventors: Robert E. Hefner, Jr., Rosharon, TX (US); Helge Braun, Lake Jackson, TX (US); Armenio Costa, Estarreja (PT); Brian Cramm, Lake Jackson, TX (US)

(73) Assignees: Dow Global Technologies LLC, Midland, MI (US); Dow Portugal Produtos Quimicos, Sociedade Unipessoal, LDA, Estarreja (PT)

( * ) Notice: Subject to any disclaimer, the term of this patent is extended or adjusted under 35 U.S.C. 154(b) by 530 days.

(21) Appl. No.: 17/426,227

(22) PCT Filed: Jan. 23, 2020

(86) PCT No.: PCT/US2020/014717
§ 371 (c)(1),
(2) Date: Jul. 28, 2021

(87) PCT Pub. No.: WO2020/163092
PCT Pub. Date: Aug. 13, 2020

(65) Prior Publication Data
US 2022/0106264 A1    Apr. 7, 2022

Related U.S. Application Data

(60) Provisional application No. 62/802,470, filed on Feb. 7, 2019.

(51) Int. Cl.
*C07C 267/00* (2006.01)
*C07C 263/10* (2006.01)
*C08G 18/76* (2006.01)
*C08G 18/79* (2006.01)

(52) U.S. Cl.
CPC .......... *C07C 267/00* (2013.01); *C07C 263/10* (2013.01); *C08G 18/7671* (2013.01); *C08G 18/797* (2013.01)

(58) Field of Classification Search
CPC ... C07C 263/10; C07C 267/00; C08G 18/025; C08G 18/725; C08G 18/7664; C08G 18/7671; C08G 18/797
See application file for complete search history.

(56) References Cited

U.S. PATENT DOCUMENTS

| | | | |
|---|---|---|---|
| 2,663,736 A | 12/1953 | McCormack | |
| 2,663,737 A | 12/1953 | McCormack | |
| 2,663,739 A | 12/1953 | McCormack | |
| 3,362,979 A * | 1/1968 | Bentley | C07C 265/12 564/333 |
| 4,014,935 A | 3/1977 | Ibbotson | |
| 4,072,712 A | 2/1978 | Meisert | |
| 4,096,334 A * | 6/1978 | Keil | C07D 307/52 564/252 |
| 4,120,884 A | 10/1978 | Woerner | |
| 4,177,205 A | 12/1979 | Schaaf | |
| 4,199,524 A | 4/1980 | Schaaf | |
| 4,260,554 A | 4/1981 | Ohlinger | |
| 4,294,719 A | 10/1981 | Wagner | |
| 4,743,626 A | 5/1988 | Narayan | |
| 2007/0213432 A1 | 10/2007 | Savino | |
| 2007/0213496 A1 | 10/2007 | Savino | |
| 2008/0021176 A1 | 1/2008 | Savino | |
| 2008/0085987 A1 | 4/2008 | Savino | |

FOREIGN PATENT DOCUMENTS

| | | | |
|---|---|---|---|
| EP | 1773755 A1 * | 4/2007 | ........... C07D 213/40 |
| EP | 1773755 B | 10/2012 | |

* cited by examiner

*Primary Examiner* — Yevgeny Valenrod
*Assistant Examiner* — Blaine G Doletski

(57) ABSTRACT

Phenyl isocyanates are removed from a solvent stream obtained from an MDI and/or PMDI manufacturing process by reaction in the presence of a carbodiimidization catalyst to form the corresponding N,N-diphenylcarbodiimides. The N,N-diphenylcarbodiimides can be recycled into the MDI and/or PMDI manufacturing process where they can react with MDI and/or PMDI to form uretonimines. The uretonimines have at most minimal effect on the properties and usefulness of the MDI and/or PMDI product and so can be left in the MDI and/or PMDI product.

9 Claims, No Drawings

PHENYL ISOCYANATE CONVERSION PROCESS

This invention relates to methods for converting phenyl isocyanates into N,N'-diphenylcarbodiimide compounds.

Diphenylmethane diisocyanate (MDI) amd polymeric MDI are produced industrially in large volumes. "Polymeric MDI" is a mixture of one or more isomers of MDI and one or more polymethylene polyphenylisocyanates (PMDI) that have at least three phenyl isocyanate groups. Their primary use is as a raw material for making polyurethane and polyurea polymers. Phenyl isocyanate typically is produced as a by-product of the manufacturing process.

The phenyl isocyanate is usually removed from the product, typically when the product is separated from the reaction solvent. This produces a stream that contains solvent, most of the phenyl isocyanate and a small quantity of MDI or polymeric MDI.

The solvent is generally recycled, but to do so the phenyl isocyanate must be removed from it so the phenyl isocyanate does not accumulate over time. Potential toxicological concerns require that the phenyl isocyanate be destroyed or converted to an innocuous product.

Some previous approaches have capitalized on the reactivity of isocyanate groups to convert phenyl isocyanate to a solid material that is easily separated from the solvent. Thus, EP 1,773,755 describes catalyzing the trimerization of phenyl isocyanate to form tris(phenyl)isocyanurate. U.S. Pat. No. 4,745,216 describes reacting the phenyl isocyanate with polymer beads that have amino or hydroxyl functionality. U.S. Pat. No. 4,405,527 describes reacting the phenyl isocyanate with stoichiometric or greater amounts of polyamine or glycols to convert it to urethanes or ureas.

All of these approaches have significant shortcomings. There is the cost of added raw materials. These added raw materials represent another source of impurities which themselves must be rigorously removed from the solvent before it is recycled, again to avoid accumulation. Water is inexpensive but tends to lead to a slow reaction with low conversions of the monoisocyanates to ureas and also tends to produce monoamine by-products, which are another source of contamination. Adding stoichiometric or greater amounts of amines as in U.S. Pat. No. 4,405,527 can be especially problematic because they often are not entirely consumed or removed. When these amines are recycled with the solvent, they engage in unwanted reactions that in some cases consume the desired polyisocyanate products, decreasing yield and forming higher molecular weight impurities that increase viscosity and modify other characteristics of the product. They present a difficult separation problem if they are to be removed. The unreacted amines also can become phosgenated to form unwanted isocyanate species that are very difficult to remove from the desired product.

Isocyanate compounds are known to form carbodiimides when reacted in the presence of certain catalysts. See, for example, U.S. Pat. Nos. 4,014,935, 4,072,712, 4,120,884, 4,177,205, 4,199,524, 4,260,554 and 4,743,626 as well as US Published Patent Application Nos. 2007-0213432, 2007-0213496, 2008-0021176 and 2008-0085987. The carbodiimides thus formed can further react with isocyanate compounds to form uretonimines. The processes described in the foregoing references mainly deal with forming carbodiimide-modified and uretonimine-modified polyisocyanate compounds for polyurethane production. The thus-modified polyisocyanate compounds often are liquids and in some cases impart some desirable properties to polyurethanes from the modified polyisocyanates.

In one aspect, this invention is an MDI and/or polymeric MDI manufacturing process, comprising the steps of:
a) reacting aniline with formaldehyde to produce a mixture of methylene dianiline (MDA), one or more polymethylene polyanilines having at least three aniline groups (PMDA) and unreacted aniline;
b) removing aniline from the mixture produced in step a) to produce a process stream containing the MDA, PMDA and residual aniline;
c) phosgenating the process stream from step b) in a non-polar solvent to form an isocyanate process stream containing the non-polar solvent, MDI, one or more polymethylene polyphenylisocyanates that have at least three phenyl isocyanate groups (PMDI) and at least one phenyl isocyanate;
d) separating MDI and PMDI from the isocyanate process stream obtained in step c) by distillation to produce a solvent stream containing the non-polar solvent, greater than zero up to 10 weight percent of the at least one phenyl isocyanate based on the weight of the solvent stream and 0 to 5 weight percent, based on the weight of the solvent stream, of MDI and/or PMDI;
e) reacting the solvent stream obtained in step d) in the presence of a catalytically effective amount of a carbodiimidization catalyst, to convert at least a portion of the at least one phenyl isocyanate to a N,N'-diphenylcarbodiimide,
f) optionally removing and/or deactivating the carbodiimidization catalyst and
g) optionally recycling the N,N'-diphenylcarbodiimide formed in step e), non-polar solvent and optionally the carbodiimidization catalyst and/or residues from the deactivation of the carbodiimidization catalyst, directly or indirectly into step d).

The invention is in another aspect a method for converting a phenyl isocyanate to an N,N'-diphenylcarbodiimide. The method comprises reacting a solution of phenyl isocyanate in a liquid non-polar solvent in the presence of an effective amount of a carbodiimidization catalyst to convert at least a portion of the phenyl isocyanate to N,N'-diphenylcarbodiimide. In preferred embodiments, the method of this aspect of the invention includes a further step of deactivating the carbodiimidization catalyst.

Steps a), b) and c) of the process of the first aspect of the invention are well-known in the art and described, for example, in U.S. Pat. Nos. 4,189,354, 4,118,410, 4,294,666, WO 1999/054289A, WO 2013/081873 and US Published Patent Application No. 2007-0117997, among many others. Aniline and aqueous formaldehyde are typically condensed in a molar ratio from about between about 20:1 and about 1.6:1. The reaction is generally acid-catalyzed. A weight ratio of aniline to acid catalyst from between about 20:1 and about 1.1:1 is useful. The temperature of the reaction mixture is typically 30° C. to 250° C. After the reaction, the reaction mixture is typically neutralized with a base, such as a hydroxide of an alkali metal or an alkaline earth metal (e.g., sodium hydroxide). In this process, a portion of the aniline is typically not converted to MDA (methylene dianiline) or polymethylene polyanilines (PMDA) and remains in the product mixture obtained from the reaction.

The reaction mixture generally includes an aqueous phase and an organic phase which contains the amines (including unreacted aniline). The phases typically are separated, and aniline removed from the organic phase using methods such as crystallization, extraction or, preferably, distillation. The distillation may be performed at a temperature at or above the boiling temperature of aniline at the pressure employed. The pressure may be atmospheric but is preferably subatmospheric.

A residual portion of the aniline typically remains in the distilled MDA and PMDA product. When this product is taken to the subsequent phosgenation step, at least some of this residual aniline is converted to phenyl isocyanate by reaction with phosgene.

The phosgenation step is performed in a non-polar solvent. The solvent is generally further characterized as having a boiling temperature (at one standard atmosphere pressure) of at least 60° C. and being (i) a solvent for MDI and/or PMDI produced in the phosgenation step, (ii) devoid of isocyanate groups and (iii) inert, i.e., non-reactive toward isocyanate groups and reaction products which form under the conditions of the process of the invention. The boiling temperature (at one standard atmosphere) in some embodiments is at least 80° C. or at least 100° C. and up to 200° C., up to 175° C. or up to 150° C. Examples of suitable solvents include halogenated aromatic compounds such as monochlorobenzene, o-dichlorobenzene, p-dichlorobenzene and m-dichlorobenzene, various trichlorobenzene isomers, mixtures thereof, and the like. Other suitable solvents include, for example, benzene, toluene, para-xylene, and various aliphatic hydrocarbons that can be halogenated or non-halogenated, mixtures of any two or more thereof, and the like.

The phosgenation may be carried out at temperatures of, for example, 50° C. to 250° C. and at pressures ranging from, for example, ambient pressure to about 50 bar. This converts MDA and PMDA to MDI and PMDI, respectively, and, as mentioned, converts residual aniline to a phenyl isocyanate.

The phenyl isocyanate produced in the phosgenation reaction is a compound having only one isocyanate group, which isocyanate group is directly bonded to a ring carbon of a benzene ring. The phenyl isocyanate may be unsubstituted, i.e., is phenyl isocyanate having the structure:

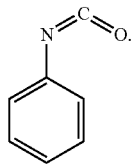

However, some halogenation or haloalkylation of aniline and/or phenyl isocyanate is sometimes experienced during the phosgenation reaction, and for that reason, the phenyl isocyanate may include not only unsubstituted phenyl isocyanate itself, but also various halogenated (particularly chlorinated) phenyl isocyanates such as 2-chlorophenyl isocyanate, 3-chlorophenyl isocyanate, and 4-chlorophenyl isocyanate; dichlorophenyl isocyanates including 2,4-dichlorophenyl isocyanate, 2,6-dichlorophenyl isocyanate, 3,4-dichlorophenyl isocyanate and 3,5-dichlorophenyl isocyanate; as well as haloalkyl-substituted (particularly chloroalkyl-substituted) phenyl isocyanates such as p-chloromethylphenyl isocyanate and o-chloromethylphenyl isocyanate. Mixtures of any two or more of the foregoing (including mixtures of phenyl isocyanate and one or more substituted phenyl isocyanates as described above) may be present in the reaction mixture produced in the phosgenation reaction.

The isocyanate process stream in some embodiments may contain, for example, a) 50 to 95 weight percent, more typically 70 to 90 weight percent or 75 to 85 weight percent non-polar solvent, 5 to 50 weight percent, especially 10 to 30 weight percent or 15 to 25 weight percent, MDI and/or PMDI and 0.01 to 100, especially 0.1 to 25 or 0.2 to 10 ppm by weight phenyl isocyanate, in all cases based on the total weight of the isocyanate process stream.

MDI and PMDI are separated from the isocyanate process stream obtained in the phosgenation step by distillation. This produces an MDI/PMDI stream, and a solvent stream containing the non-polar solvent, greater than zero up to 10 weight percent of at least one phenyl isocyanate based on the weight of the solvent stream and 0 to 5 weight percent, based on the weight of the solvent stream, of MDI and/or PMDI.

The phenyl isocyanate(s) preferably are present in the solvent stream as a somewhat dilute solution in the solvent(s). The organic solvent(s) may constitute, for example, at least 90% of the solvent stream. In particular embodiments, the organic solvent(s) may constitute at least 95% of the weight thereof, and may constitute up to 99.995%, up to 99.9%, up to 99.8%, up to 99.5%, up to 99% or up to 98.5% thereof.

The phenyl isocyanate(s) may constitute, for example, up to 10%, up to 5%, up to 4% or up to 3% of the weight of the solvent stream. In particular embodiments the phenyl isocyanate(s) constitute at least 0.005%, at least 0.01%, at least 0.2%, at least 0.5%, at least 1% or at least 1.5% of the weight of the solvent stream.

The solvent stream may further include other isocyanate compounds, including one or more polyisocyanate compounds, which may not be completely separated from the organic solvent(s) during the distillation step (d). Of particular interest are MDI (diphenylmethane diisocyanate), which may be any one or more of the 2,2'-; 2,4'- or 4,4'-isomers, and one or more polymethylene polyphenylisocyanates that have at least three phenyl isocyanate groups, as well as polymeric MDI. Also useful are any of the foregoing that are modified with urea, urethane, carbodiimide, uretdione, allophanate and/or biuret groups. It is preferred that the other organic isocyanate(s), if present at all, be present in relatively small quantities compared to the phenyl isocyanate(s). The other organic isocyanate(s), if present at all, may constitute at least 0.0001%, at least 0.1%, at least 0.2%, at least 0.5%, at least 1% or at least 1.5% of the weight of the solvent stream, and may constitute up to 5%, up to 4%, or up to 3% thereof.

The solvent stream obtained in step d) of the process is reacted in the presence of a catalyically effective amount of a carbodiimidization catalyst, to convert at least a portion of the at least one phenyl isocyanate to an N,N'-diphenylcarbodiimide.

Examples of carbodiimidization catalysts include, for example, phospholene compounds; phospholidine compounds such as phospholidine oxides; phosphate esters; phosphine oxides; diaza- and oxaza-phospholanes and phosphorinanes; triaryl arsines; arsine oxides; metallic derivatives of acetylacetone; metal complexes derived from a d-group transition element and a T-bonding ligand; and urea, biuret, amide, imide and/or anilide compounds.

Useful phospholene compounds include compounds represented by any one of the structures:

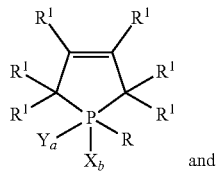

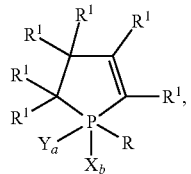

wherein:
a=b and are 0 or 1;
R is unsubstituted or inertly substituted hydrocarbyl;
each $R^1$ is independently hydrogen, halogen, unsubstituted or inertly substituted hydrocarbyl having up to 20 carbon atoms; and
when a=b=1, X and Y each are halogen, especially chlorine or bromine, or X and Y together are =O or =S.

When X and Y are halogen, the phospholene compound is referred to herein as a phospholene halide. When X and Y together are =O and =S, the compounds are referred to herein as phospholene oxides and phospholene sulfides, respectively.

Useful phospholidine compounds include those represented by the structure:

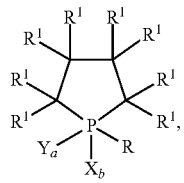

wherein R, each $R^1$, X, Y, a and b are as defined with regard to structures I and II above. As before, when X and Y are halogen, the compound is referred to herein as a phospholidine halide and when X and Y together are =O and =S, the compounds are referred to herein as phospholidine oxides and phospholidine sulfides, respectively.

In each of structures I, II and III, X and Y preferably together are =O; a and b each are preferably 1; R is preferably $C_{1-4}$ alkyl (such as methyl, ethyl, n-propyl, isopropyl, n-butyl, t-butyl and sec-butyl), phenyl, benzyl or ethylphenyl; and each $R^1$ is preferably independently hydrogen, linear or branched $C_{1-8}$ (especially $C_{1-6}$) alkyl or alkenyl (such as methyl, ethyl, n-propyl, isopropyl, n-butyl, t-butyl, sec-butyl, pentenyl, butenyl, propenyl, allyl, 4-methyl-3-pentenyl), benzyl, phenyl or ethylbenzyl.

Other suitable phospholene and phospholidine catalysts include those described in U.S. Pat. Nos. 2,663,736, 2,663,737, 2,663,738, 2,663,739, 4,014,935, 4,120,884, 4,260,554, and 4,743,626, Specific examples of phospholene catalysts include 1-phenyl-3-methyl-2-phospholene-1-oxide; 1-phenyl-3-methyl-3-phospholene-1-oxide; 1-phenyl-3-methyl-2-phospholene-1-sulfide; 1-phenyl-3-methyl-3-phospholene-1-sulfide; 1-phenyl-3-methyl-2-phospholene-1,1-dichloride; 1-phenyl-3-methyl-3-phospholene-1,1-dichloride; 1-benzyl-3-methyl-2-phospholene-1-oxide; 1-benzyl-3-methyl-3-phospholene-1-oxide; 1-benzyl-3-methyl-2-phospholene-1-sulfide; 1-benzyl-3-methyl-3-phospholene-1-sulfide; 1-benzyl-3-methyl-2-phospholene-1,1-dichloride; 1-benzyl-3-methyl-3-phospholene-1,1-dichloride; 1-phenyl-2-phospholene-1-oxide; 1-phenyl-3-phospholene-1-oxide; 1-phenyl-2-phospholene-1-sulfide; 1-phenyl-3-phospholene-1-sulfide; 1-phenyl-2-phospholene-1,1-dichloride; 1-phenyl-3-phospholene-1,1-dichloride; 1-methyl-3-phospholene-1-oxide; 1-methyl-2-phospholene-1-oxide; 1-methyl-3-phospholene-1-sulfide; 1-methyl-2-phospholene-1-sulfide; 1-methyl-3-phospholene-1,1-dichloride; 1-methyl-2-phospholene-1,1-dichloride; 1-ethyl-3-phospholene-1-oxide; 1-ethyl-2-phospholene-1-oxide; 1-ethyl-3-phospholene-1-sulfide; 1-ethyl-2-phospholene-1-sulfide; 1-ethyl-3-phospholene-1,1-dichloride; 1-ethyl-2-phospholene-1,1-dichloride; 1-ethyl-3-methyl-2-phospholene-1-oxide; 1-ethyl-3-methyl-3-phospholene-1-oxide; 1-ethyl-3-methyl-2-phospholene-1-sulfide; 1-ethyl-3-methyl-3-phospholene-1-sulfide; 1-ethyl-3-methyl-2-phospholene-1,1-dichloride; 1-ethyl-3-methyl-3-phospholene-1,1-dichloride; 1-ethylphenyl-3-methyl-2-phospholene-1-oxide; 1-ethylphenyl-3-methyl-3-phospholene-1-oxide; 1-ethylphenyl-3-methyl-2-phospholene-1-sulfide; 1-ethylphenyl-3-methyl-3-phospholene-1-sulfide; 1-ethylphenyl-3-methyl-2-phospholene-1,1-dichloride; 1-ethylphenyl-3-methyl-3-phospholene-1,1-dichloride; 3-(4-methyl-3-pentenyl)-1-phenyl-2-phospholene-1-oxide; 3-(4-methyl-3-pentenyl)-1-phenyl-3-phospholene-1-oxide; 3-(4-methyl-3-pentenyl)-1-phenyl-2-phospholene-1-sulfide; 3-(4-methyl-3-pentenyl)-1-phenyl-3-phospholene-1-sulfide; 3-(4-methyl-3-pentenyl)-1-phenyl-2-phospholene-1,1-dichloride; 3-(4-methyl-3-pentenyl)-1-phenyl-3-phospholene-1,1-dichloride; 3-chloro-1-phenyl-2-phospholene-1-oxide; 3-chloro-1-phenyl-3-phospholene-1-oxide; 3-chloro-1-phenyl-2-phospholine-1-sulfide; 3-chloro-1-phenyl-3-phospholene-1-sulfide; 3-chloro-1-phenyl-2-phospholene-1,1-dichloride; 3-chloro-1-phenyl-3-phospholene-1,1-dichloride; 1,3-diphenyl-2-phospholene-1-oxide; 1, 3-diphenyl-3-phospholene-1-oxide; 1, 3-diphenyl-2-phospholene-1-sulfide; 1,3-diphenyl-3-phospholene-1-sulfide; 1,3-diphenyl-2-phospholene-1,1-dichloride; 1,3-diphenyl-3-phospholene-1,1-dichloride and mixtures of any two or more thereof.

Specific examples of phospholidine catalysts include 1-phenyl phospholidine; 1-benzyl phospholidine; 1-ethyl phospholidine; 1-phenyl-3-phospholidine; 3-methyl-1-phenyl-3-phospholidine; 1-ethyl-3-phospholidine; 3-isopropyl-1-phenyl-3-phospholidine; 3-(4-methyl-3-pentenyl)-1-phenyl-3-phospholidine and mixtures of any two or more thereof.

Representative examples of diaza- and oxaza-phospholanes and phosphorinanes compounds are 2-ethyl-1,3-dimethyl-1,3,2-diazaphospholane-2-oxide; 2-chloromethyl-1,3-dimethyl-1,3,2-diaza-pholane-2-oxide; 2-trichloromethyl-1,3-dimethyl-1,3,2-diazaphospholane-2-oxide; 2-phenyl-1,3-dimethyl-1,3,2-diazaphospholane-2-oxide; 2-phenyl-1,3-dimethyl-1,3,2-diaza-phosphorinane-2-oxide; 2-benzyl-1,3-dimethyl-1,3,2-diazaphospholane-2-oxide; 2-allyl-1, 3-dimethyl-1,3,2-diazaphospholane-2-oxide; 2-bromomethyl-1,3-dimethyl-1,3,2-diazaphospholane-2-oxide; 2-cyclohexyl-1,3-dimethyl-1,3, 2-diazaphospholane-2-oxide; 2-(2-ethoxyethyl)-1,3-dimethyl-1,3,2-diazaphospholane-2-oxide; 2-naphthyl-1,3-dimethyl-1, 3, 2-diazaphospholane-2-oxide and mixtures of any two or more thereof.

Phospholene and phospholidine catalysts may be used in conjunction with a phosphite co-catalyst as described in US Published Patent Application No. 2007/0213432. Examples of such phosphite co-catalysts include triphenyl phosphite, trialkyl (linear or branched, having up to 20 carbon atoms) phosphites such as tributyl phosphite, monophenyl dialkyl (linear or branched, having up to 20 carbon atoms) phosphites such as diisodecyl phosphite, and diphenyl monoalkyl (linear or branched, having up to 20 carbon atoms) phosphites such as diphenyl isodecyl phosphite.

Suitable triaryl arsines and arsine oxides include those described in U.S. Pat. Nos. 3,406,198, 4,143,063 and 4,743,626, and include, for example, triphenylarsine, tris(p-tolyflarsine, tris(methoxyphenyflarsine, tris(p-ethoxyphenyflarsine, tris(p-chlorophenyl)arsine, tris(p-fluorophenyl)arsine, tris(2,5-xylyflarsine, tris(pcyanophenyl)arsine, tris(1-naphthyl) arsine, tris(p-methylmercaptophenyflarsine, tris(p-biphenyl)arsine, p-chlorophenyl bis(p-tolyl)arsine, phenyl(p-chlorophenyl)(p-bromophenyl)arsine, triphenylarsine oxide, triethylarsine oxide, and polymer bound arsine oxides.

Suitable metallic derivatives of acetylacetone include, for example, beryllium, aluminum, zirconium, chromium and iron acetylacetonates as described, for example, in U.S. Pat. No. 3,152,131.

Examples of suitable phosphate esters include trimethylphosphate, triethylphosphate, ethyldipropylphosphate, triisopropylphosphate, triallylphosphate, triphenylphosphate, and tricresylphosphate.

Examples of suitable phosphine oxides include triethylphosphine oxide, tributylphosphine oxide, triphenylphosphine oxide, and tris(chloromethyl)phosphine oxide.

Examples of suitable metal complexes derived from a d-group transition element and a T-bonding ligand include iron pentacarbonyl, diiron pentacarbonyl, tungsten hexacarbonyl, molybdenum hexacarbonyl, chromium hexacarbonyl, dimanganese decacarbonyl, nickel tetracarbonyl, ruthenium pentacarbonyl and iron tetracarbonylmethylisocyanide complex.

Suitable urea, biuret, amide, imide and/or anilide compounds include those described in U.S. Pat. No. 4,072,712, such as urea, monomethylurea, N,N-dimethylurea, N,N'-diethylurea, N,N'-diethyl-N-methylthiourea, diphenylurea, diphenylthiourea, N-methyl-N'-dimethylurea, N-phenyl-N'-ethylurea, phenylthiourea, N,N-diphenyl-N'-dimethylurea, tetramethylurea, 1,3,5-triphenylbiuret, 1,3-diphenyl-5,5-dimethylbiuret, 1,3-diphenyl-allophanic acid methyl ester, formanilide, acetamide, methylacetamide, dimethylacetamide, propionic acid morpholide, bis(benzoyl)piperazine, benzoylpiperazine, benzoyl piperidine, benzanilide, acetanilide, N-ethylbenzanilide, chloroacetamide, thioacetamide, thiobutyric acid anilide, maleic acid hydrazide, caprolactam, N-methylcaprolactam, dodecane-12-lactam, phthalimide, isatin, 1,2,3,6-tetrahydrophthalimide, naphtholactam-1,8 2-pyrrolidone, piperazine-2,5-dione, saccharin, barbituric acid, diethylbarbituric acid, rhodamine, vinyl acetamide, p-toluene-sulphonylurea, N-phenylsulphonyl-N'-methylurea, N-phenyl-sulphonyl-N'-phenylurea, phenylsulphonyl-N,N'-diphenylurea, 4-acetyl-aminobenzene-sulphonylurea, acetylpropionylurea or acetylbenzoylurea, N-acetyl-N-methylurea, benzoylthiourea, N-propionyl-N'-phenylurea, dimethoxyphosphonoform-N-methylanilide, diethoxyphosphonoform anilide, diethoxyphosphonoform naphthylamide, and bis-(2-chloroethoxy)-phosphonoform-N-methylanilide.

The catalyst is used in a catalytically effective amount, which may vary somewhat according to the particular catalyst selected. In some embodiments, the amount of catalyst is at least 0.00025 mole or at least 0.001 mole per mole of the phenyl isocyanates. The amount of catalyst in some embodiments is up to 0.02 mole, up to 0.01 mole, up to 0.005 mole or up to 0.0025 mole per mole of the phenyl isocyanates. The foregoing amounts have been found to be particularly advantageous for phospholene and phospholidine catalysts. Greater amounts can be used but generally offer little advantage. Smaller amounts may lead to unduly long reaction times.

Phenyl isocyanates are converted to N,N'-diphenylcarbodiimides by contacting the phenyl isocyanate-containing solvent stream with the catalyst for a time and temperature sufficient to effect the conversion of at least some of the phenyl isocyanate to the corresponding N,N'-diphenylcarbodiimide. An elevated temperature is preferred, such as at least 80° C., at least 100° C. or at least 120° C. The elevated temperature may be, for example, up to 250° C., up to 200° C., up to 175° C. or up to 150° C. The reaction time may vary widely, depending on parameters such as catalyst concentration, the particular catalyst, temperature, starting concentration of phenyl isocyanates and the desired conversion to carbodiimides. In some embodiments, the reaction time is at least 10 minutes, at least 30 minutes or at least one hour and up to 10 hours, up to 8 hours, up to 6 hours or up to 5 hours.

Reaction pressures may be atmospheric, subatmospheric or superatmospheric. The pressure should be high enough such that the organic isocyanate and solvent do not significantly volatilize at the reaction temperature. The reaction pressure may be, for example, at least 0.1 atmosphere, at least 0.5 atmosphere, at least 0.9 atmosphere and, for example, up to 10 atmospheres, up to 5 atmospheres, up to 2 atmospheres or up to 1.25 atmospheres. The reaction preferably is performed under an inert atmosphere such as nitrogen, helium or argon.

In some embodiments, at least 50 mole-percent, at least 75 mole-percent, at least 90 mole-percent or at least 95 mole-percent of the phenyl isocyanates are converted to carbodiimides. Higher conversions are preferred so phenyl isocyanate does not accumulate or have to be recycled in the process. Up to 100% or up to 99.9% of the phenyl isocyanate can be so converted. A portion of the N,N'-diphenylcarbodiimides thus formed may react further with an isocyanate group to form uretonimine compounds. If this takes place, it is preferred that fewer than 10 mole-percent of the carbodiimides react in this way.

A N,N'-diphenylcarbodiimide product having the structure:

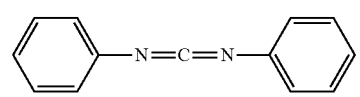

(IV)

is produced when the phenyl isocyanate starting compound is unsubstituted. When the phenyl isocyanate starting compound is substituted as described above, the resulting carbodiimide compound will be substituted correspondingly on one or both of the phenyl rings. Thus, either or both of the phenyl rings of structure IV may be substituted with one or more halogen and/or haloalkyl substituents. When a mixture of phenyl isocyanate starting compounds is present, a corresponding mixture of N,N'-diphenylcarbodiimide products is produced.

Some or all of the N,N'-diphenylcarbodiimides thus produced, together with some or all of the polar solvent and optionally the carbodiimidization catalyst and/or residues from the deactivation of the carbodiimidization catalyst, are recycled directly or indirectly into step d) of the process (i.e., the step of separating MDI and/or PMDI from the phosgenation solution). By "indirectly" it is meant the materials are recycled into one or more of steps a), b) or c) of the process and pass through the process into step d), or otherwise undergo one or more processing steps before being recycled into step d). "Direct" recycling means the materials are recycled into step d) without being recycled into any of steps a), b) and c) or undergoing any other processing steps before being recycled.

It is preferred to remove and/or deactivate the carbodiimidization catalyst before the recycling step, to prevent the build-up of active catalyst and to avoid carbodiimidization reactions involving MDI and/or PMDI from occurring.

As mentioned, the N,N'-diphenylcarbodiimide can engage in further reactions with isocyanate groups to form uretonimines. When the carbodiimides are recycled, they in some embodiments form uretonimines with MDI or PMDI. Even though few, if any, uretonimines form in the carbodiimidization step, the recycled N,N'-diphenylcarbodiimides readily tend to form uretonimines with MDI and/or PMDI when recycled, mostly likely due to the higher concentration of isocyanate groups that are present in the isocyanate process stream fed into step d) of the process compared to the solvent stream obtained from step d). Therefore, although uretonimine formation tends to be quite small during the carbodiimization step e), the recycled N,N'-diphenylcarbodiimides have been found to react readily when recycled into step d) of the process to form uretonimines. Furthermore, this reaction does not require the presence of active carbodiimidization catalyst residues. The uretonimines thus formed stay almost entirely with the MDI and/or PMDI that is separated from the isocyanate process stream in step d), so the resulting solvent stream contains at most negligible quantities thereof.

The minor amount of uretonimines formed in the MDI or PMDI product have a negligible, if any, effect on properties of the product, such as viscosity, isocyanate content and isocyanate functionality. The uretonimines formed from the recycled N,N'-diphenylcarbodiimides, unlike those formed when they react with phenyl isocyanate, typically have one or more free isocyanate groups. This is a further advantage in that those isocyanate-containing uretonimine compounds can react into the polymer when the polyisocyanate product is used to produce polymers such as polyurethanes and/or polyureas. Inasmuch as the amount of those isocyanate-containing uretonimine compounds is generally very small, this has at most a small effect on polymer properties.

The manner of catalyst removal or deactivation is not especially critical and is in general selected with reference to the particular catalyst. Among the suitable methods of removal include, for example, volatilization, absorption, precipitation, filtration and the like. Among the suitable methods of deactivation are thermal and chemical deactivation methods.

In some embodiments, phosphorene and phospholidine catalysts are deactivated by adding a "stopper" or "quenching agent", i.e., chemical deactivator, to the reaction mixture obtained in step e) of the process. Suitable "stopper" compounds are described, for example, in U.S. Published Patent Application No. 2007-0213432, 2007-0213496, 2008-0021176 and 2008-0085987.

Suitable stoppers for phospholene and/or phospholidine catalysts include Lewis acids such as, for example, phosphorus oxychloride, cadmium chloride, zinc chloride, tin (II) chloride, iron (III) chloride; carboxylic acid chlorides such as p-toluic acid chloride, benzoyl chloride, acetyl chloride, benzenesulfonyl chloride, oxalyl chloride, adipoyl chloride, sebacyl chloride and carbonyl chloride; aromatic sulfonic acid esters such as methylbenzenesulfonate, ethylbenzenesulfonate, ethyl p-toluene sulfonate and methyl p-toluenesulfonate; and alkyl sulfates such as diethyl sulfate and dimethyl sulfate; inorganic and organic acids carboxylic and/or sulfonic acids such as perchloric acid, trifluoromethanesulfonic acid, hydrochloric acid, peracetic acid, acetic acid, oxalic acid, citric acid, formic acid, ascorbic acid, benzoic acid, sulfuric acid, toluenesulfonic acid, and trifluoroacetic acid; and chloroformates such as methyl chloroformate, ethyl chloroformate, isopropyl chloroformate, n-butyl chloroformate, isopropyl chloroformate, n-butyl chloroformate, sec-butyl chloroformate and diethylene glycol bischloroformate.

A suitable amount of stopper is a molar ratio of catalyst to stopper of 1:2 to about 1:500, preferably from 1:5 to about 1:350.

In addition to the foregoing, stopper pairs such as described in US Published Patent Application No. 2007-0213496 are useful. Such a pair includes a first stopper that has a pKa greater than the second stopper. The first stopper preferably is a first acid or acid generator having a pKa of greater than about −8.0, selected from at least one inorganic acid, carboxylic acid, peroxide, sulfinic acid, sulfonic acid, sulfonic acid halide and carboxylic acid halide. Specific examples include hydrochloric acid, methanesulfonic acid, toluenesulfonic acid, sulfuric acid, sulfonic acid, acetic acid, oxalic acid, citric acid, formic acid, ascorbic acid, benzoic acid, thiophenol, peracetic acid, benzoyl chloride, and mixtures thereof. The second stopper is selected from at least one of trifluoromethanesulfonic acid and perchloric acid.

Useful stoppers for phosphine oxide carbodiimidization catalysts include, for example, magnesium chloride hydrate, stannous chloride and trichlorosilane.

Deactivation of a phospholene and/or phospholidine carbodiimidization catalyst may be performed at an elevated temperature, such as, for example, at least 50° C., at least 60° or at least 75° C. The elevated temperature may be, for example, up to 150° C., up to 125° C. or up to 100° C. The stopper may be contacted with the reaction mixture from step e) at such temperatures for a period ranging from 5 minutes to 10 hours or more, as may be needed to deactivate the catalyst. As before, reaction pressures are preferably such that the solvent does not significantly volatilize and the deactivation step is preferably performed under an inert atmosphere.

In a preferred process, the nonpolar solvent containing the N,N'-diphenylcarbodiimide compound(s) is recycled directly or indirectly into step d) of the process, with the resulting process stream containing process solvent (including the recycled solvent), MDI, PMDI, phenyl isocyanate, N-N'-diphenylcarbodiimide compound(s) being subjected to a distillation step as described before. The distillation step results in a substantially solvent-free (less than 80 ppm solvent, for example) polyisocyanate composition containing MDI and/or PMDI and the uretonimine reaction products of the N,N'-diphenylcarbodiimide(s).

The weight ratio of N,N'-diphenylcarbodiimide compound(s) recycled to step d) (and in the MDI and/or PMDI-containing process stream obtained from step d)) to MDI and PMDI should be low, such as 0.001 to 5 parts by weight of N,N'-diphenylcarbodiimide compounds per 100 parts by weight of MDI and PMDI combined. A more preferred amount is 0.005 to 2.5 parts, 0.005 to 1.5 parts, 0.005 to 1 part or 0.005 to 0.025 parts, on the same basis.

The N,N'-diphenylcarbodiimide(s), when recycled into the MDI and/or PMDI manufacturing process in small amounts as described above and converted to the corresponding uretonimines, have little effect on the properties and utilities of the MDI and/or PMDI products. Depending on the amount of N,N-diphenylcarbodiimide(s) recycled into the MDI and/or PMDI, product viscosities are increased slightly if at all. Molecular weights ($M_n$, $M_w$, $M_z$) and polydispersities (all as measured by GPC against 1000 molecular weight polyethylene glycol standards) all increase slightly, if at all. Isocyanate content and functionality decrease slightly, if at all.

It is also within the scope of the invention to separate the N,N'-diphenylcarbodiimide compound(s) from the solvent after step e) and dispose or otherwise use them without recycling them into step d) of the process. N,N'-diphenylcarbodiimide compound(s) may be separated from the solvent by any convenient separation techniques such as decantation, filtration, vacuum filtration, centrifugation, flocculation, precipitation, distillation, or settling.

The N,N'-diphenylcarbodiimide compound(s) separated from the organic solvent may be discarded, burned or otherwise disposed of, or used in some manner. By converting phenyl isocyanates to N,N'-diphenylcarbodiimide compounds, or by further converting said carbodiimide compounds to uretonimines contained in a MDI or PMDI product, toxicological and other concerns associated with the handing and disposal of the isocyanates are at least partially alleviated.

The following examples are provided to illustrate the invention, but are not intended to limit the scope thereof. All parts and percentages are by weight unless otherwise indicated.

EXAMPLES 1 AND 2 AND COMPARATIVE SAMPLE A

A. A 2% solution of phenyl isocyanate in monochlorobenzene is prepared. A 0.0266% solution of 3-methyl-1-phenyl-2-phospholene-1-oxide (MPPO) in monochlorobenzene is separately prepared. The solutions are combined at 20° C. and under nitrogen to produce a reaction mixture initially containing 11.15 millimoles of phenyl isocyanate and 0.0166 millimole of catalyst. The starting weight ratio of MPPO catalyst to phenyl isocyanate is 0.0024:1; the mole ratio is 0.0015:1. With stirring, the reaction mixture is heated to reflux (132° C.) over 30 minutes and held at that temperature for 4 hours. A clear, colorless solution is obtained and maintained at room temperature. Phenyl isocyanate is undetectable by gas chromatography. N,N'-diphenylcarbodiimide is present, as confirmed by GC-MS analysis, but dimerized phenyl isocyanate and phenyl isocyanate uretonimine are not detected.

When step A is repeated using only 0.00026 millimoles of catalyst per millimole of phenyl isocyanate, the carbodiimidization reaction proceeds more slowly, with N,N'-diphenylcarbodiimide and residual phenyl isocyanate (0.026 wt. %) being present after 4 hours heating at reflux.

B. To deactivate the catalyst, 0.016 g of tin (II) chloride is added to 78 g of the product from step A at about 38° C., followed by 0.954 g of benzoyl chloride. The resulting solution is heated to 80° C. over 26 minutes, becoming orange in color. Heating at 80° C. is continued another 5 hours.

Deactivation of the catalyst is confirmed by combining a 10.18 g aliquot of the resulting solution with 0.178 g of phenyl isocyanate at 20° C. The resulting solution is heated to 80° C. over 12 minutes, held at that temperature for 40 minutes, heated further to reflux over 17 minutes and held at that temperature for an hour. No decrease in phenyl isocyanate concentration is seen by GC analysis.

C. A 20 g aliquot of the solution containing the deactivated catalyst from step B is heated at 70° C. under 3.7 mm Hg pressure to distill off the solvent, leaving 0.38 g of N,N'-diphenylcarbodiimide that contains residues from the deactivated catalyst. Under nitrogen, at 22° C., this material is combined with 37.3 g of a polymeric MDI. The resulting mixture is heated to 80° C. over 22 minutes, held at that temperature for 13 minutes, heated further to 100° C. over 10 minutes and held at that temperature for 30 minutes. A transparent amber solution is obtained. Isocyanate content is 31.2%. This product is designated Ex. 1. The reaction of carbodiimides with PMDI to form uretonimines is confirmed by MALDI-TOF/TOF CID MS analysis, showing a precursor ion, $C_{44}H_{30}N_6NaO_4^-$, containing 3 isocyanate moieties and one uretonimine moiety, at 729.22207 Daltons and another precursor ion, $C_{36}H_{25}N_5NaO_3^-$, containing 2 isocyanate moieties and one uretonimine moiety, at 597.1771 Daltons. These correspond to uretonimines formed from one molecule of N,N'-diphenylcarbodiimide with four-ring and three-ring PMDI molecules, respectively.

A 10 g aliquot of the solution containing the deactivated catalyst from step B. is heated at 70° C. under 1.6 mm Hg pressure to distill off the solvent, leaving 0.15 g of N,N'-diphenylcarbodiimide that contains residues from the deactivated catalyst. Under nitrogen, at 23° C., this material is combined with 37.3 g of a polymeric MDI. The resulting mixture is heated to 80° C. over 10 minutes, held at that temperature for 13 minutes, heated further to 100° C. over 9 minutes and held at that temperature for 30 minutes. A transparent amber solution is obtained. Isocyanate content is 31.6%. This product is designated Ex. 2.

For comparison, polymeric MDI (36.9 g) is heated by itself under nitrogen to 80° C. over 16 minutes, held at that temperature for 22 minutes, heated further over 9 minutes to 100° C. and held at that temperature for 30 minutes. Isocyanate content is 31.7%, which is not meaningfully different than obtained in the case in which N,N'-diphenylcarbodiimide with deactivated catalyst residues is combined with the polymeric MDI and heated. This product is designated Comp. Sample A.

The isocyanate content of the untreated polymeric MDI is 31.4%. Thus, the heating step in either case (with or without the N,N'-diphenylcarbodiimide and deactivated catalyst residues) has minimal effect on isocyanate content. In particular, the catalyst residues are shown not to have any meaningful catalytic activity.

The viscosities of each of Examples 1 and 2 and Comparative Sample A are measured at 25.6° C. and 100° C. using a TA Instruments AR-2000 cone-and-plane Rheometer using a 3° C./minute heat-up rate, a 40 mm cone and a 54 μm gap. Molecular weights and polydispersities are determined by GPC against a 1000 MP polyethylene glycol standard. Results are as indicated in the following table:

| | Viscosity, Pa · s | | |
|---|---|---|---|
| Temperature | Ex. 1 | Ex. 2 | Comp. A* |
| 25.6° C. | 0.23 | 0.20 | 0.20 |
| 100° C. | 0.009 | 0.010 | 0.009 |
| $M_n$ | 456 | 452 | 452 |
| $M_w$ | 593 | 584 | 583 |
| PDI | 1.30 | 1.29 | 1.29 |

*Comparative

These results show that minimal viscosity and molecular weight changes are seen when N,N'-diphenylcarbodiimide containing deactivated catalyst residue is combined with polymeric MDI and heated to as high as 100° C. to form uretonimine.

Due to the lack of solvent and therefore higher concentrations of polymeric MDI and catalyst residues, the conditions employed in part C above are more stringent than would be seen in the case in which the carbodiimide- and catalyst residue-containing solution is recycled into step d) of the inventive process. Nonetheless, negligible reaction and negligible changes in properties, compared to the unmodified polymeric MDI product are seen. This data indicates that the process solution containing the N,N'-diphenylcarbodiimides and deactivated catalyst residue are suitable for recycling back into the MDI and/or PMDI manufacturing process.

COMPARATIVE SAMPLE B

A. A 2 wt. % solution of phenyl isocyanate in monochlorobenzene is prepared. A 0.0266% solution of MPPO in monochlorobenzene is separately prepared. The solutions are combined at 20° C. and under nitrogen to produce a reaction mixture initially containing 5.5 millimoles of phenyl isocyanate and 0.0083 millimole of catalyst. With stirring, the reaction mixture is heated to reflux (132° C.) over 15 minutes and held at that temperature for 3.8 hours. A clear, colorless solution is obtained and maintained at room temperature. Phenyl isocyanate is undetectable by gas chromatography. N,N'-diphenylcarbodiimide is present, but dimerized phenyl isocyanate and phenyl isocyanate uretonimine are not detected.

B. 6.016 grams of the MPPO solution from A above are combined with 30.08 grams of fresh 2 wt. % phenyl isocyanate solution in monochlorobenzene. Phenyl isocyanate content by gas chromatography is 1.64 wt. %. The solution is held at 21° C. for 90 minutes, after which the phenyl isocyanate content is measured at 1.63 wt. %. The solution is heated to reflux over 14 minutes, and held at that temperature for 2 hours, at which time the phenyl isocyanate content is reduced to 0.87 wt. %.

This experiment simulates the effect of recycling the N,N'-diphenylcarbodiimide solution without deactivating the catalyst. In this experiment, the fresh phenyl isocyanate stands in for MDI and/or PMDI to make the progress of the reaction easier to follow by gas chromatography. The continued consumption of phenyl isocyanate indicates that the catalyst remains active, even when diluted greatly, when combined with the fresh phenyl isocyanate solution. The activity of the catalyst indicates that unwanted carbodiimidization formation would be expected if the N,N'-diphenylcarbodiimide were to be recycled into an MDI and/or PMDI manufacturing process without catalyst deactivation.

When this experiment is repeated, this time combining 2.048 grams of the MPPO solution from A. with 32.05 grams of fresh 2 wt. % phenyl isocyanate solution, phenyl isocyanate consumption is still seen, decreasing from 1.80 wt. % to 1.25 wt. % after 3.7 hours at reflux. This shows that even greater dilution is not adequate to overcome the presence of the active catalyst residues.

What is claimed is:

1. An MDI and/or polymeric MDI manufacturing process, comprising the steps of:
   a) reacting aniline with formaldehyde to produce a mixture of methylene dianiline (MDA), one or more polymethylene polyanilines having at least three aniline groups (PMDA) and unreacted aniline;
   b) removing aniline from the mixture produced in step a) to produce a process stream containing the MDA, PMDA and residual aniline;
   c) phosgenating the process stream from step b) in a non-polar solvent to form an isocyanate process stream containing the non-polar solvent, MDI, one or more polymethylene polyphenylisocyanates that have at least three phenyl isocyanate groups (PMDI) and at least one phenyl isocyanate;
   d) separating the MDI and PMDI from the isocyanate process stream obtained in step c) by distillation to produce a solvent stream containing the non-polar solvent, greater than zero up to 10 weight percent of the at least one phenyl isocyanate based on the weight of the solvent stream and 0 to 5 weight percent, based on the weight of the solvent stream, of the MDI and/or PMDI;
   e) reacting the solvent stream obtained in step d) in the presence of a catalytically effective amount of a carbodiimidization catalyst, to convert at least a portion of the at least one phenyl isocyanate to an N,N'-diphenylcarbodiimide;
   f) optionally removing and/or deactivating the carbodiimidization catalyst; and
   g) recycling the N, N'-diphenylcarbodiimide formed in step e), optionally the nonpolar solvent and optionally the carbodiimidization catalyst and/or residues from the deactivation of the carbodiimidization catalyst, directly or indirectly into step d).

2. The manufacturing process of claim 1 wherein the carbodiimization catalyst is one or more of a phospholene compound; a phospholidine compound; a phosphate ester; a phosphine oxide; a diazaphospholane; an oxaza-phospholane; a diazaphosphorinane; an oxazaphosphorinane; a triaryl arsine; an arsine oxide; a metallic derivative of acetylacetone; a metal complex derived from a d-group transition element and a T-bonding ligand; a urea compound; a biuret compound; an amide compound; an imide compound; and an anilide compound.

3. The manufacturing process of claim 2 wherein the carbodiimization catalyst is a phospholidine.

4. The manufacturing process of claim 2 wherein the carbodiimization catalyst is a phospholidine oxide.

5. The manufacturing process of claim 2 wherein the carbodiimization catalyst is a phospholene oxide.

6. The manufacturing process of claim 2 wherein step f) is performed and is performed by adding a chemical deactivator.

7. The manufacturing process of claim 6 wherein the chemical deactivator includes a Lewis acid.

8. The manufacturing process of claim 7 wherein the Lewis acid includes tin(II) chloride.

9. The manufacturing process of claim 1 wherein the N,N'-diphenylcarbodiimide recycled in step d) reacts with the MDI and/or the PMDI to form one or more uretonimine compounds.

* * * * *